(12) United States Patent
Sone

(10) Patent No.: US 11,751,754 B2
(45) Date of Patent: Sep. 12, 2023

(54) OBJECTIVE OPTICAL SYSTEM, IMAGE PICKUP APPARATUS, ENDOSCOPE AND ENDOSCOPE SYSTEM

(71) Applicant: OLYMPUS CORPORATION, Hachioji (JP)

(72) Inventor: Nobuhiko Sone, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 550 days.

(21) Appl. No.: 17/026,570

(22) Filed: Sep. 21, 2020

(65) Prior Publication Data

US 2021/0093172 A1    Apr. 1, 2021

Related U.S. Application Data

(63) Continuation of application No. PCT/JP2018/030467, filed on Aug. 17, 2018.

(30) Foreign Application Priority Data

Mar. 22, 2018    (JP) .................. 2018-055089

(51) Int. Cl.
  *A61B 1/00*       (2006.01)
  *G02B 15/14*      (2006.01)
  *G02B 23/24*      (2006.01)

(52) U.S. Cl.
  CPC ...... *A61B 1/00188* (2013.01); *A61B 1/00096* (2013.01); *G02B 15/143507* (2019.08); *G02B 23/2438* (2013.01)

(58) Field of Classification Search
  CPC ............ A61B 1/00188; A61B 1/00096; A61B 1/00174; A61B 1/051; G02B 15/143507; G02B 23/2438; G02B 23/243; G02B 23/2446

USPC ................ 600/176, 167, 160, 173, 109, 168
See application file for complete search history.

(56) References Cited

U.S. PATENT DOCUMENTS

| | | | |
|---|---|---|---|
| 7,292,395 B2 | 11/2007 | Noda | |
| 9,459,443 B2 | 10/2016 | Uzawa et al. | |
| 10,036,883 B2 | 7/2018 | Fujii | |
| 10,088,666 B2 | 10/2018 | Nasu et al. | |
| 2007/0070523 A1 | 3/2007 | Noda | |
| 2015/0042773 A1 | 2/2015 | Uzawa et al. | |

(Continued)

FOREIGN PATENT DOCUMENTS

| | | | |
|---|---|---|---|
| JP | 2007093961 A | 4/2007 | |
| JP | 2012037768 A | 2/2012 | |
| JP | 5607278 B1 | 10/2014 | |

(Continued)

OTHER PUBLICATIONS

International Preliminary Report on Patentability (IPRP) (and English language translation thereof) dated Oct. 1, 2020 issued in counterpart International Application No. PCT/JP2018/030467.

(Continued)

*Primary Examiner* — Ryan N Henderson
*Assistant Examiner* — Pamela F Wu
(74) *Attorney, Agent, or Firm* — Holtz, Holtz & Volek PC

(57) ABSTRACT

An objective optical system includes, in order from an object: a first lens group having a negative refractive power, a second lens group having a positive refractive power, and a third lens group having a positive refractive power. The second lens group includes an aperture stop and moves at a time of changing magnification.

11 Claims, 9 Drawing Sheets

(56) References Cited

U.S. PATENT DOCUMENTS

2018/0003944 A1  1/2018  Fujii
2018/0017779 A1  1/2018  Nasu et al.

FOREIGN PATENT DOCUMENTS

WO   2017043352 A1   3/2017
WO   2017145264 A1   8/2017

OTHER PUBLICATIONS

International Search Report (ISR) (and English translation thereof) dated Oct. 16, 2018 issued in International Application No. PCT/JP2018/030467.
Written Opinion dated Oct. 16, 2018 issued in International Application No. PCT/JP2018/030467.

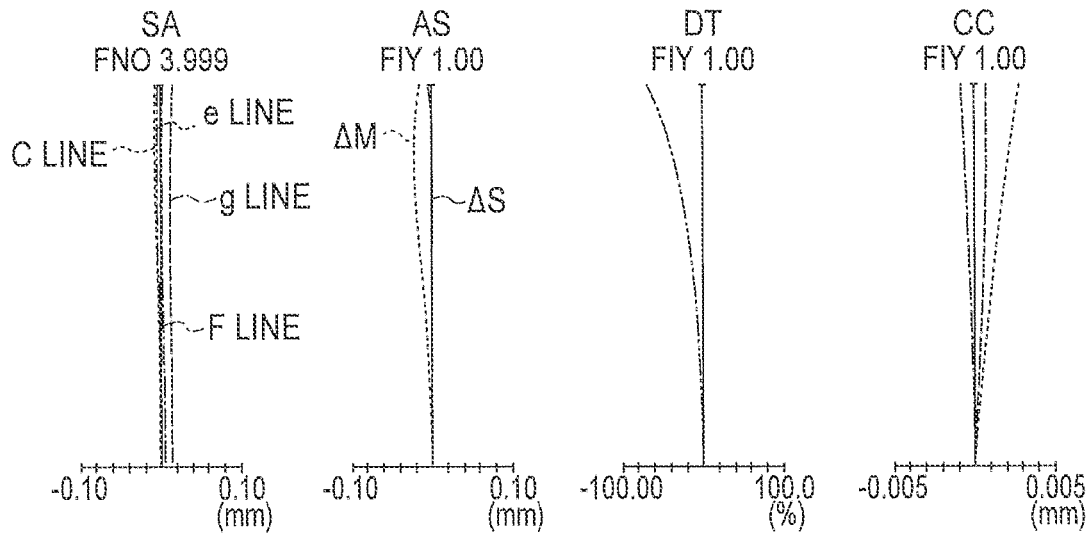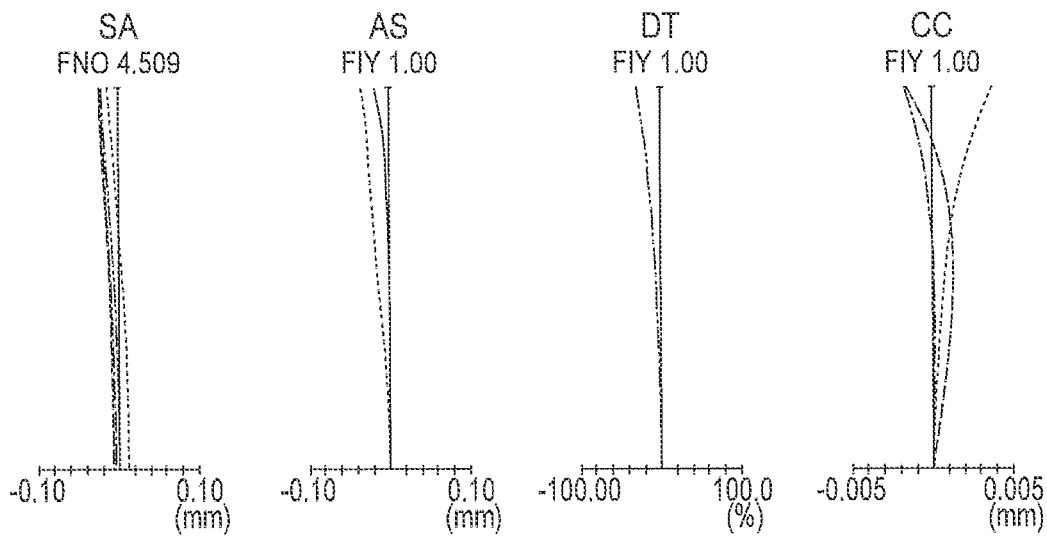

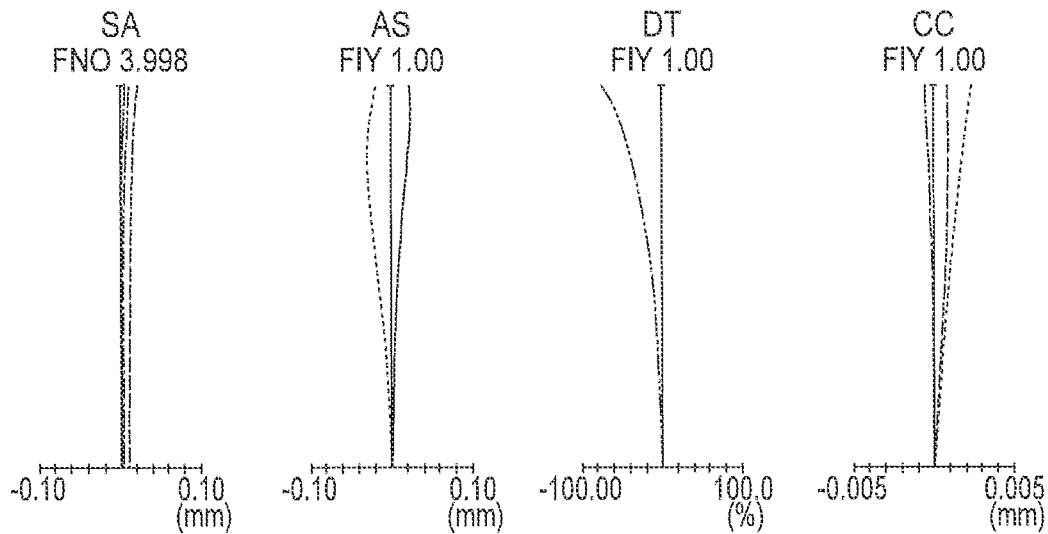
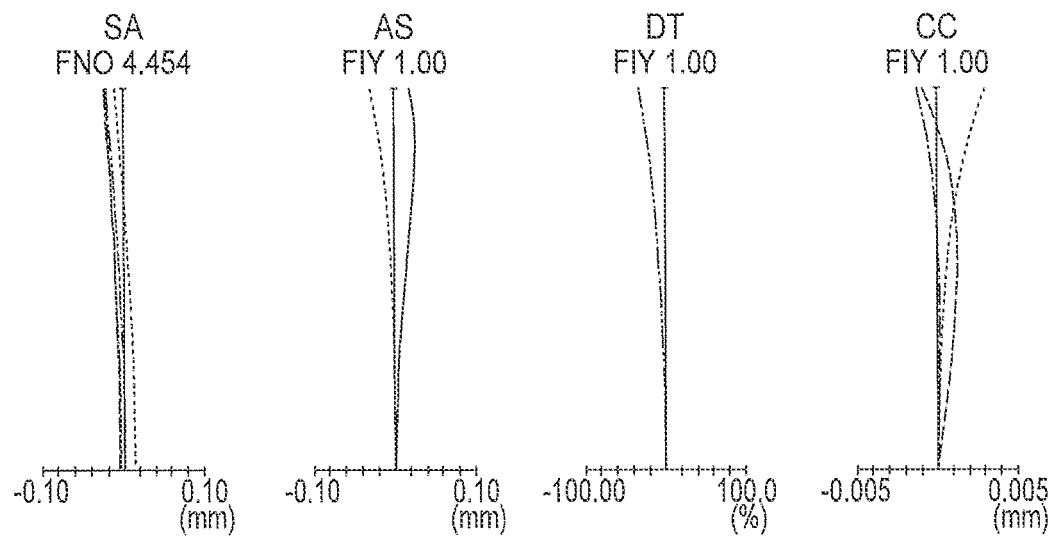

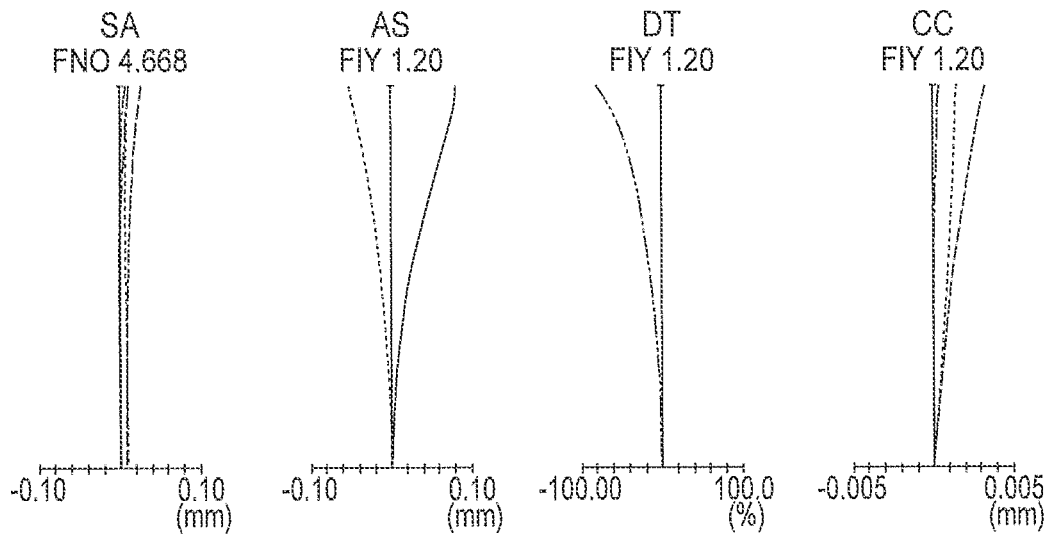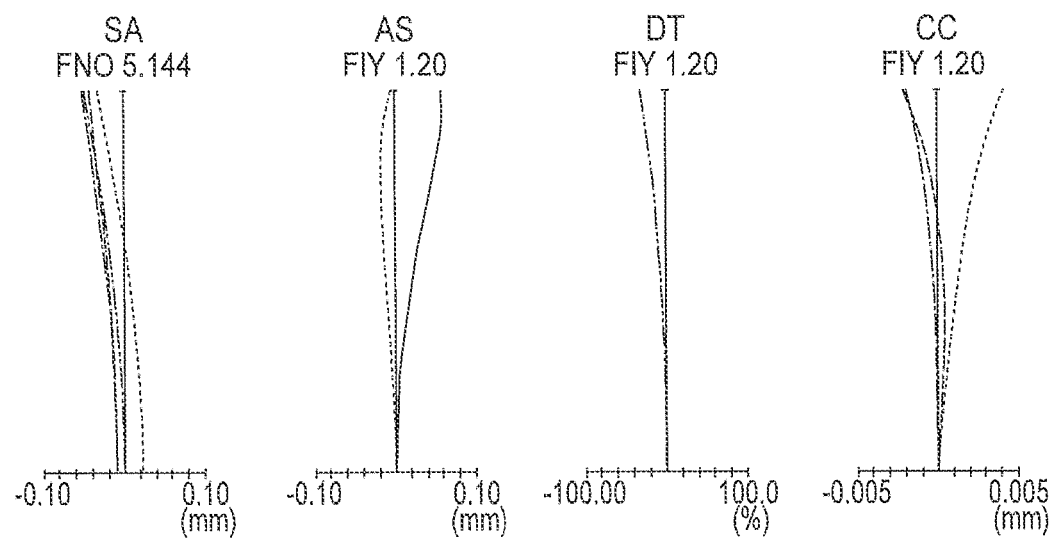

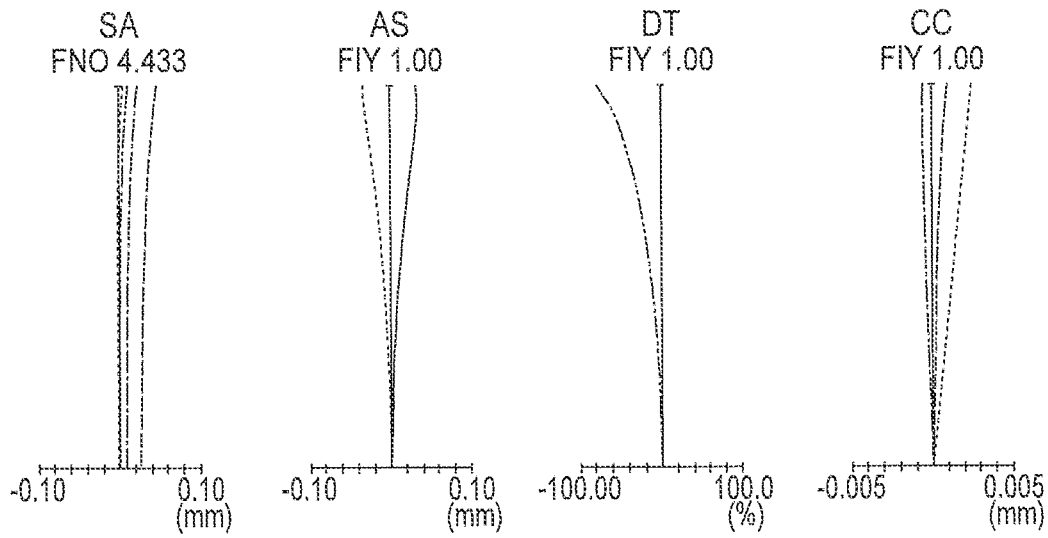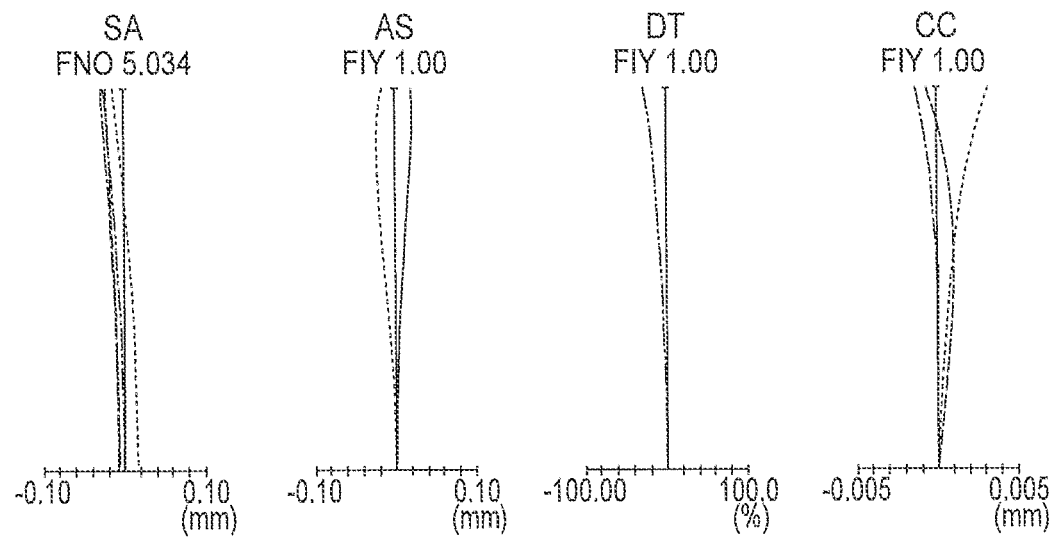

OBJECTIVE OPTICAL SYSTEM, IMAGE PICKUP APPARATUS, ENDOSCOPE AND ENDOSCOPE SYSTEM

CROSS-REFERENCE TO RELATED APPLICATION

The present application is a continuation application of PCT/JP2018/030467 filed on Aug. 17, 2018 which is based upon and claims the benefit of priority from Japanese Patent Application No. 2018-055089 filed on Mar. 22, 2018; the entire contents of which are incorporated herein by reference.

BACKGROUND

Technical Field

The present disclosure relates to an objective optical system, an image pickup apparatus, an endoscope and an endoscope system.

Description of the Related Art

In medical endoscopes, a magnifying observation is used for observing a lesion site. To observe the lesion site by the magnifying observation, the lesion site needs to be found. In the magnifying observation, an observation range is narrower than that of a conventional observation (hereinafter referred to as "normal observation"). Therefore, it is not easy to find the lesion site using the magnifying observation. Thus, it is desirable that a single objective optical system be able to perform the normal observation and the magnifying observation.

In the magnifying observation, a distance from the objective optical system to an object position (hereinafter referred to as "object distance") is, for example, about 2 mm. The object distance in the normal observation is, however, much longer than 2 mm.

If the optical system is configured to make the object position in the normal observation and the focus position of the objective optical system coincident with each other, an object image in the normal observation (referred to as "normal image") becomes an in-focus image.

However, an object position in the magnifying observation is apart from an object position in the normal observation. In addition, the object position in the magnifying observation is not within the depth of field of the objective optical system in the normal observation. As a result, in the optical system in which the normal image is in an in-focus state, an object image in the magnifying observation (hereinafter referred to as "magnifying image") does not become an in-focus image.

To produce an in-focus object image in the magnifying observation, the objective optical system may have a focusing function. If the objective optical system has the focusing function, it is possible to produce both the normal image and the magnifying image in the in-focus state.

An objective optical system having a focusing function is disclosed in Japanese Patent No. 5607278. The objective optical system includes in order from an object side to an image side: a front group having a negative refractive power, a focusing lens, and a rear group having a positive refractive power. The focusing lens moves at a time of focusing.

SUMMARY

An objective optical system according to at least some embodiments of the present disclosure includes, in order from an object side:
a first lens group having a negative refractive power,
a second lens group having a positive refractive power, and
a third lens group having a positive refractive power, wherein:
the second lens group includes an aperture stop and moves at a time of changing magnification, and
following conditional expressions (1), (3) and (4) are satisfied:

$$1 < (Lb \times f3)/(Lf \times f12) < 9 \tag{1}$$

$$1 < |f1/f3| < 20 \tag{3; and}$$

$$1 < |f1/f2| < 14 \tag{4}$$

where
Lb denotes a distance from a surface nearest to the object side of the third lens group to an image plane,
f3 denotes a focal length of the third lens group,
Lf denotes a distance from a surface nearest to the object side of the first lens group to the surface nearest to the object side of the third lens group,
f12 denotes a combined focal length of the first lens group and the second lens group at a wide angle end,
f1 denotes a focal length of the first lens group, and
f2 denotes a focal length of the second lens group.

An image pickup apparatus and an endoscope according to at least some embodiments of the present disclosure include the aforementioned objective optical system.

An endoscope system according to at least some embodiments of the present disclosure includes: the aforementioned objective optical system, and an image processor.

BRIEF DESCRIPTION OF THE DRAWINGS

FIG. 3A, FIG. 3B, FIG. 3C, FIG. 3D, FIG. 3E, FIG. 3F, FIG. 3G, and FIG. 3H are aberration diagrams of the objective optical system for an endoscope according to Example 1;

FIG. 5A, FIG. 5B, FIG. 5C, FIG. 5D, FIG. 5E, FIG. 5F, FIG. 5G, and FIG. 5H are aberration diagrams of the objective optical system for an endoscope according to Example 2;

FIG. 7A, FIG. 7B, FIG. 7C, FIG. 7D, FIG. 7E, FIG. 7F, FIG. 7G, and FIG. 7H are aberration diagrams of the objective optical system for an endoscope according to Example 3;

FIG. 9A, FIG. 9B, FIG. 9C, FIG. 9D, FIG. 9E, FIG. 9F, FIG. 9G, and FIG. 9H are aberration diagrams of the objective optical system for an endoscope according to Example 4.

DETAILED DESCRIPTION

Figure 1A:
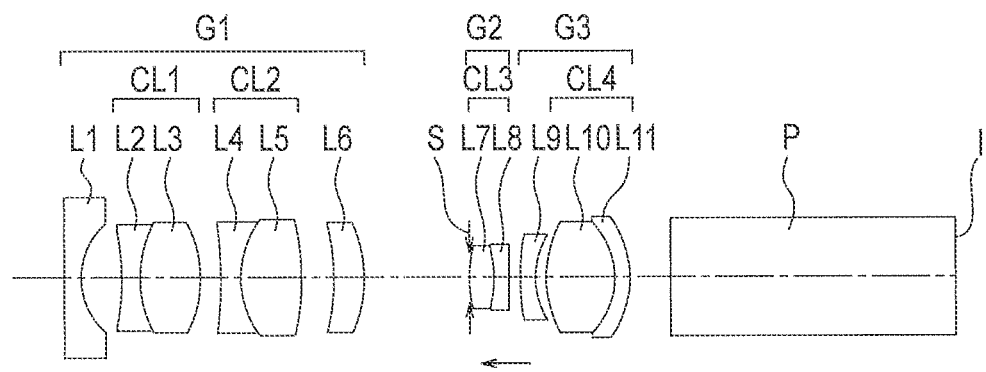
FIG. 1A and FIG. 1B are diagrams illustrating a specific configuration of an objective optical system for an endoscope of the present embodiment.

An embodiment and examples of an objective optical system for an endoscope according to the present disclosure will be explained hereinafter in detail on the basis of the drawings. The present disclosure is not limited to the embodiment and examples. In the following explanations, an objective optical system for an endoscope is used as an example of an objective optical system.

An objective optical system for an endoscope according to the present embodiment can perform the normal observation and the magnifying observation by a single optical system, in endoscope observation. To implement this, in the objective optical system for an endoscope according to the present embodiment, the optical system includes a plurality of lens groups and one of the lens groups moves on an optical axis. In the following explanations, for convenience, a state in the normal observation takes a wide-angle end and a state in the magnifying observation takes a telephoto end.

The objective optical system for an endoscope according to the present embodiment includes, in order from an object side: a first lens group having a negative refractive power, a second lens group having a positive refractive power, and a third lens group having a positive refractive power, the second lens group includes an aperture stop and moves at a time of changing magnification, and following conditional expression (1) is satisfied:

$$1 < (Lb \times f3)/(Lf \times f12) < 9 \quad (1)$$

where
Lb denotes a distance from a surface nearest to the object side of the third lens group to an image plane,
f3 denotes a focal length of the third lens group,
Lf denotes a distance from a surface nearest to the object side of the first lens group to the surface nearest to the object side of the third lens group, and
f12 denotes a combined focal length of the first lens group and the second lens group at a wide angle end.

For securing a long back focal distance, it is important to make order of refractive powers appropriate and to balance optical path lengths. Furthermore, particularly in an optical system with a long back focal length, it is difficult to suppress increase in astigmatism. Accordingly, it is important to correct the astigmatism favorably.

To secure a long back focal length and achieve favorable correction of the astigmatism, when the objective optical system for an endoscope is divided into a front group and a rear group, it is preferable that both refractive powers of the front group and the rear group have positive refractive powers. In addition, it is preferable that the optical length of the front group and the optical length of the rear group have well balance.

The objective optical system for an endoscope of the present embodiment has the front group including the first lens group having a negative refractive power and the second lens group having a positive refractive power, and has the rear group including the third lens group having a positive refractive power. By applying such a configuration, it is possible to correct favorably the astigmatism generated in the first lens group and the second lens group by the third lens group while securing a long back focal length.

The objective optical system for an endoscope of the present embodiment has the aforementioned configuration and satisfies the conditional expression (1). By satisfying the conditional expression (1), it is possible to further favorably correct the astigmatism.

Both the distance from the surface nearest to the object side of the third lens group to the image plane and the distance from the surface nearest to the object side of the first lens group to the surface nearest to the object side of the third lens group are distances without air conversion.

When a value falls below a lower limit value of the conditional expression (1), the refractive power of the third lens group is excessively large. For this reason, correction of the astigmatism becomes excessive or it is not possible to secure a back focal length sufficiently.

When a value exceeds an upper limit value of conditional expression (1), the correction effect of the astigmatism in the third lens group weakens or large astigmatism is generated in the first lens group and the second lens group. Therefore, it becomes difficult to correct the astigmatism with the third lens group. Furthermore, it is possible to secure a back focal length, but secured amount is excessive.

It is preferable that the following conditional expression (1') be satisfied, instead of the conditional expression (1).

$$1.5 < (Lb \times f3)/(Lf \times f12) < 6 \quad (1')$$

It is preferable that the following conditional expression (1'') be satisfied, instead of the conditional expression (1).

$$2 < (Lb \times f3)/(Lf \times f12) < 4 \quad (1'')$$

Figure 1B:
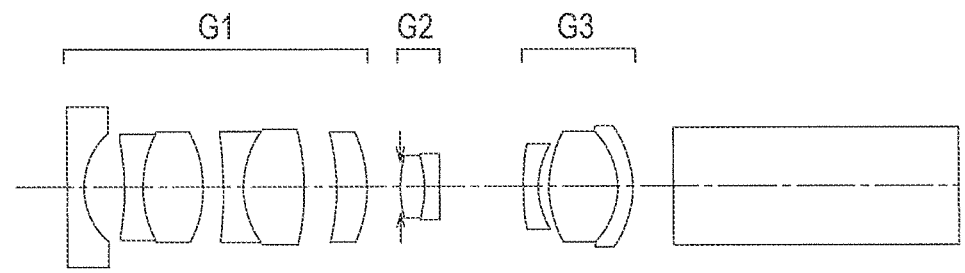
Figure 1C:
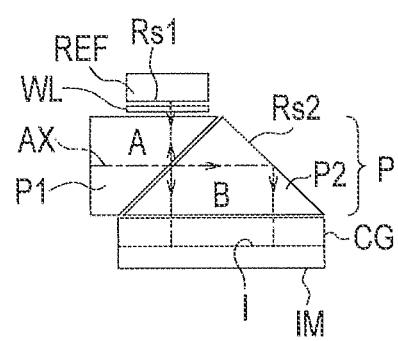
FIG. 1C is a sectional view illustrating a specific configuration of a prism.
Figure 2A:
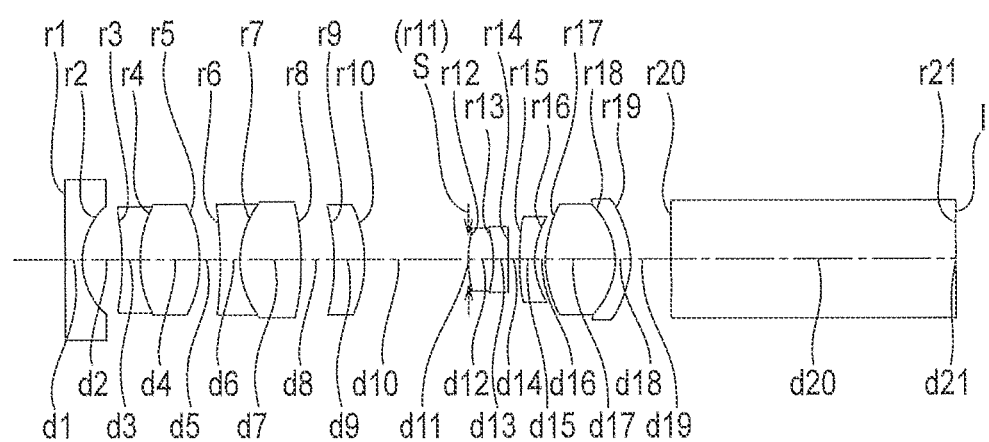
FIG. 2A and FIG. 2B are sectional views of a lens of an objective optical system for an endoscope according to Example 1.
Figure 2B:
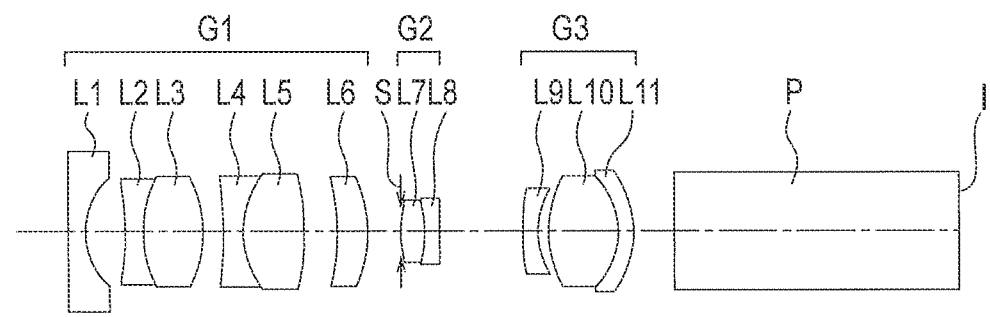
Figure 4A:
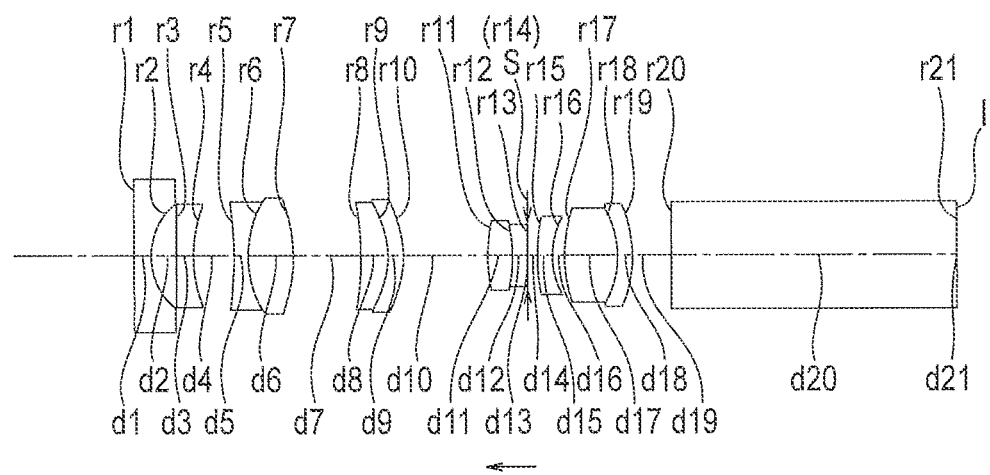
FIG. 4A and FIG. 4B are sectional views of a lens of an objective optical system for an endoscope according to Example 2.
Figure 4B:
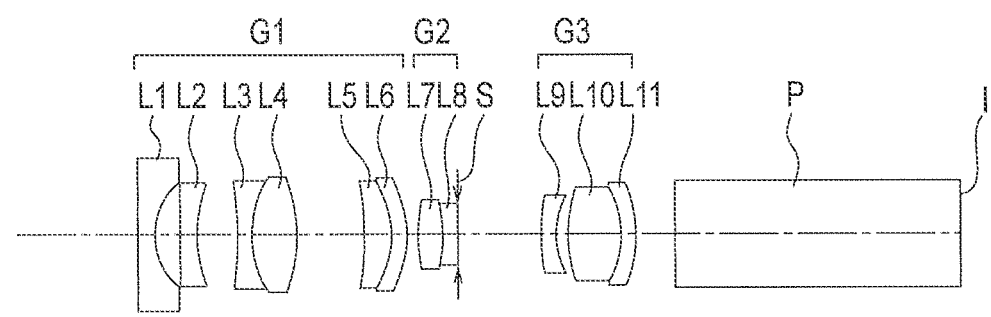
Figure 6A:
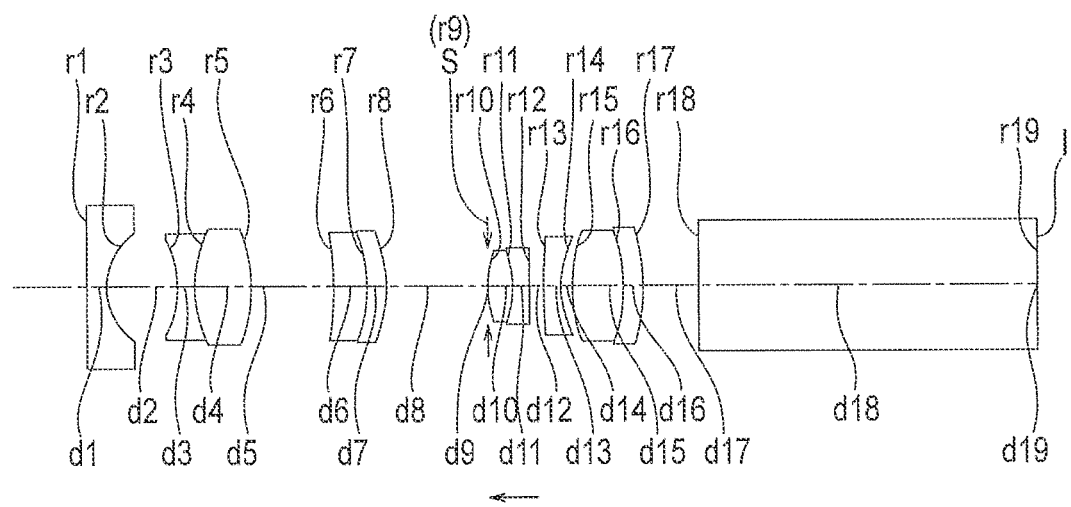
FIG. 6A and FIG. 6B are sectional views of a lens of an objective optical system for an endoscope according to Example 3.
Figure 6B:
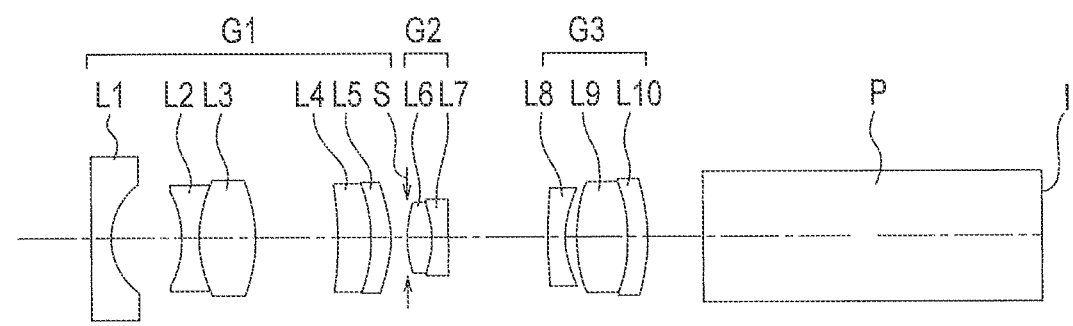
Figure 8A:
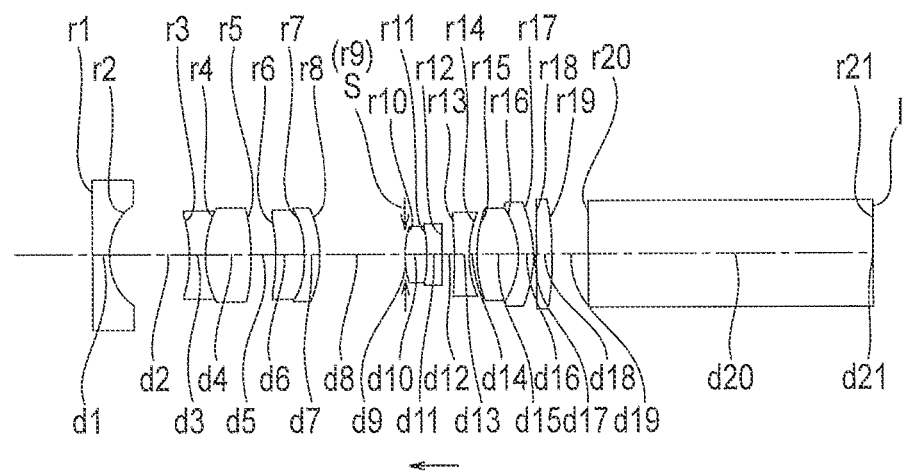
FIG. 8A and FIG. 8B are sectional views of a lens of an objective optical system for an endoscope according to Example 4.
Figure 8B:
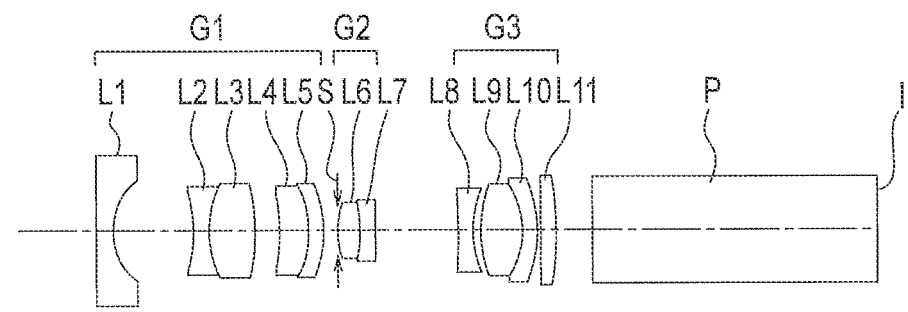

A specific configuration example for a basic configuration will be described. FIG. 1 is sectional views illustrating a specific configuration of the objective optical system in the present embodiment and a sectional view illustrating a specific configuration of a prism. FIG. 1A is a sectional view of the objective optical system for an endoscope at a wide angle end, FIG. 1B is a sectional view of the objective optical system for an endoscope at a telephoto end, and FIG. 1C is a sectional view of a prism.

The objective optical system for an endoscope includes, in order from an object side: a first lens group G1 having a negative refractive power, a second lens group G2 having a positive refractive power, and a third lens group G3 having a positive refractive power. An aperture stop S is disposed between the first lens group G1 and the second lens group G2. More specifically, the aperture stop S is disposed near a surface nearest to the object side of the second lens group G2.

The first lens group G1 includes, in order from the object side: a negative first lens L1, a negative second lens L2, a positive third lens L3, a negative fourth lens L4, a positive fifth lens L5, and a positive sixth lens L6. The second lens L2 and the third lens L3 are cemented to form a cemented lens CL1. The fourth lens L4 and the fifth lens L5 are cemented to form a cemented lens CL2.

The second lens group G2 includes a positive seventh lens L7 and a negative eighth lens L8. The seventh lens L7 and the eighth lens L8 are cemented to form a cemented lens CL3.

The third lens group G3 includes, in order from the object side: a negative ninth lens L9, a positive tenth lens L10, and a negative eleventh lens L11. The tenth lens L10 and the eleventh lens L11 are cemented to form a cemented lens CL4.

Changing magnification is carried out by moving the second lens group G2. The second lens group G2 moves toward the object side at a time of changing magnification from the wide angle end to the telephoto end. Since a distant object is in focus at the wide angle end, it is possible to perform the normal observation. Since a close object is in focus at the telephoto end, it is possible to perform magnifying observation. The aperture stop S moves together with the second lens group G2.

A prism P is disposed on the image side of the third lens group G3. An image pickup element (not illustrated) is disposed on the image side of the prism P. The image side surface of the prism P is an image plane I. The image pickup surface of the image pickup element coincides with the image side surface of the prism P.

When a cover glass is provided to the image pickup element, the cover glass is placed on the image side of the prism P. Thus, the image side surface of the cover glass becomes the image plane I. Accordingly, in this case, the thickness of the prism P is determined by taking the thickness of the cover glass into consideration.

As illustrated in FIG. 1C, the prism P includes a first prism P1 and a second prism P2. The first prism P1 and the second prism P2 are cemented with a bonding agent, for example.

Light emerged from the objective optical system for an endoscope enters the first prism P1 along an optical axis AX. Part of the light having entered the first prism P1 is reflected on a cemented surface and travels along an optical path A. The remaining light passes through the cemented surface and travels along an optical path B. In this manner, two optical paths are formed at the prism P.

The light traveling in the optical path A passes through a quarter-wave plate WL and reaches a reflection element REF. The light having reached the reflection element REF is reflected on a reflection surface Rs1. The reflected light passes through the quarter-wave plate WL, the first prism P1, the cemented surface, the second prism P2, and a parallel plate CG, and then reaches the image plane I.

The light traveling in the optical path B reaches a reflection surface Rs2 of the second prism P2. The light having reached the reflection surface Rs2 is reflected on the reflection surface Rs2. The reflected light passes through the second prism P2 and the parallel plate CG, and then reaches the image plane I.

An image pickup surface of an image pickup element IM is on the position of the image plane I. On the image pickup surface, the position of the optical path A and the optical path B are formed side by side. Accordingly, two optical images are formed on the image pickup surface side by side. The length of the optical path A is different from the length of the optical path B. Accordingly, two optical images having different in-focus positions are formed on the image pickup surface. The two optical images are captured by the image pickup element IM.

By the capture by the image pickup element IM, it is possible to obtain images of two optical images. By combining the two images, an image having a deep focal depth can be obtained.

In the objective optical system for an endoscope according to the present embodiment, it is preferable that following conditional expression (2) be satisfied:

$$4 < f3/fw < 24 \quad (2)$$

where
f3 denotes the focal length of the third lens group, and
fw denotes a focal length of the objective optical system for an endoscope at the wide angle end.

The focal length of the third lens group, in particular, largely contributes to securing a sufficient back focal length. Accordingly, it is important to design the focal length of the third lens group appropriately.

When a value falls below a lower limit value of conditional expression (2), the refractive power of the third lens group is large. For this reason, it is impossible to secure a sufficient back focal length.

When a value exceeds an upper limit value of conditional expression (2), a back focal length is unnecessarily long. For this reason, the total length of the optical system at the wide angle end becomes long.

It is preferable that the following conditional expression (2') be satisfied, instead of the conditional expression (2).

$$4.8 < f3/fw < 16 \quad (2')$$

It is preferable that the following conditional expression (2") be satisfied, instead of the conditional expression (2).

$$5.5 < f3/fw < 8 \quad (2")$$

In the objective optical system for an endoscope according to the present embodiment, it is preferable that following conditional expressions (3) and (4) be satisfied:

$$1 < |f1/f3| < 20 \quad (3); \text{ and}$$

$$1 < |f1/f2| < 14 \quad (4)$$

where
f1 denotes a focal length of the first lens group,
f2 denotes a focal length of the second lens group, and
f3 denotes the focal length of the third lens group.

Large aberrations generated in the first lens group are to be corrected by the second lens group and the third lens group. Large chromatic aberration is generated particularly in the first lens group. For this reason, with respect to longitudinal chromatic aberration, it is important to appropriately determine the refractive power of the first lens group, the refractive power of the second lens group, and the refractive power of the third lens group.

When values fall below lower limit values of both the conditional expression (3) and the conditional expression (4), the longitudinal chromatic aberration is not sufficiently corrected. For this reason, imaging performance deteriorates.

When values exceed upper limit values of both the conditional expression (3) and the conditional expression (4), correction of the longitudinal chromatic aberration becomes excessive. Furthermore, correction balance of other aberrations besides the longitudinal chromatic aberration deteriorates.

It is preferable that the following conditional expression (3') be satisfied, instead of the conditional expression (3).

$$2 < |f1/f3| < 10 \quad (3')$$

It is preferable that the following conditional expression (3") be satisfied, instead of the conditional expression (3).

$$3 < |f1/f3| < 8 \quad (3")$$

It is preferable that the following conditional expression (4') be satisfied, instead of the conditional expression (4).

$$2 < |f1/f2| < 7 \quad (4')$$

It is preferable that the following conditional expression (4") be satisfied, instead of the conditional expression (4).

$$3 < |f1/f2| \leq 5 \quad (4")$$

In the objective optical system for an endoscope according to the present embodiment, it is preferable that the first lens group include at least two cemented lenses.

In the first lens group, large chromatic aberration of magnification is generated particularly in the lens positioned nearest to the object side. Since a height of an off-axial ray is high in the third lens group, the chromatic aberration of magnification generated in the first lens group can be corrected by the third lens group. When the chromatic aberration of magnification generated in the first lens group is large, refractive power of the third lens group needs to be large to correct the aberration favorably.

However, in the optical system with a long back focal length, if the refractive power of the third lens group is made large, the outer diameter of the third lens group becomes large. Accordingly, it is not preferable to make the refractive power to the third lens group large.

For this reason, in the objective optical system for an endoscope according to the present embodiment, at least two cemented lenses are disposed in the first lens group. With this configuration, it is possible to use one of the cemented lenses for correcting the chromatic aberration of magnification and use the other cemented lens for correcting the chromatic aberration of magnification, the astigmatism, and coma. As a result, while correcting the chromatic aberration of magnification generated in the lens positioned nearest to the object side favorably, it is also possible to correct the other aberrations favorably.

In the objective optical system for an endoscope according to the present embodiment, it is preferable that the first lens group include a first cemented lens and a second cemented lens, the first cemented lens be positioned nearest to the object side, the second cemented lens be positioned nearest to the image side, and following conditional expression (5) be satisfied:

$$0.2 < |fc2/fc1| < 6.0 \tag{5}$$

where
fc1 denotes a focal length of the first cemented lens, and
fc2 denotes a focal length of the second cemented lens.

In the cemented lenses included in the first lens group, the first cemented lens is positioned nearest to the object side. In the cemented lenses included in the first lens group, the second cemented lens is positioned nearest to the image side. Accordingly, a single lens may be disposed on the object side of the first cemented lens or the image side of the second cemented lens.

When a value falls below a lower limit value of conditional expression (5), the chromatic aberration of magnification is excessive. When a value exceeds an upper limit value of conditional expression (5), the chromatic aberration of magnification can not sufficiently corrected.

It is preferable that the following conditional expression (5') be satisfied, instead of the conditional expression (5).

$$0.6 < |fc2/fc1| < 4.6 \tag{5'}$$

It is preferable that the following conditional expression (5") be satisfied, instead of the conditional expression (5).

$$1.4 < |fc2/fc1| < 3.0 \tag{5''}$$

In the objective optical system for an endoscope according to the present embodiment, it is preferable that following conditional expression (6) be satisfied:

$$2 < f3/ft < 20 \tag{6}$$

where
f3 denotes the focal length of the third lens group, and
ft denotes a focal length of the objective optical system for an endoscope at the telephoto end.

In the objective optical system for an endoscope according to the present embodiment, the focal length of the whole optical system is changed by moving the second lens group. With this configuration, improvement of the imaging performance at the telephoto end, in other words, improvement of the imaging performance in the magnifying observation is achieved.

It is noted that, if the focal length of the whole optical system at the telephoto end is not appropriate, it is difficult to maintain the total length and the back focal length of the optical system at the wide angle end, also at the telephoto end. If the total length and the back focal length are forcibly maintained, aberration deteriorate.

When a value falls below a lower limit value of conditional expression (6), the refractive power of the third lens group becomes large. For this reason, it is not possible to secure a sufficient back focal length. When a value exceeds an upper limit value of conditional expression (6), a back focal length is unnecessarily long. For this reason, the total length of the optical system is long.

It is preferable that the following conditional expression (6') be satisfied, instead of the conditional expression (6).

$$3 < f3/ft < 15 \tag{6'}$$

It is preferable that the following conditional expression (6") be satisfied, instead of the conditional expression (6).

$$4 < f3/ft < 7 \tag{6''}$$

In the objective optical system for an endoscope according to the present embodiment, it is preferable that the following conditional expressions (7) and (8) be satisfied:

$$f1/fw < -3 \tag{7; and}$$

$$f1/ft < -2 \tag{8}$$

where
f1 denotes the focal length of the first lens group,
fw denotes the focal length of the objective optical system for an endoscope at the wide angle end, and
ft denotes the focal length of the objective optical system for an endoscope at the telephoto end.

Magnification of the optical system changes as the focal length changes. When a magnification at the telephoto is made large, magnifying observation is achieved easily. For making the magnification at the telephoto end large, A refractive power of the second lens group may be made large.

However, if the refractive power of the second lens group is made large, correction of aberrations becomes difficult. Moreover, the magnification sensitivity of the second lens group becomes high. In this case, for example, influence on the controllability of operation of changing magnification cannot be ignored.

The first lens group is involved for change in magnification of the optical system. For this reason, the refractive power of the second lens group is not changed but the refractive power of the first lens group is made small. With this configuration, the refractive power of the second lens group is made relatively large. As a result, magnification at the telephoto end can be made large.

Moreover, since the refractive power of the second lens group is not changed, it is possible to maintain favorable correction of aberrations and favorable controllability of the operation of changing magnification.

When values fall below upper limit values of both the conditional expression (7) and the conditional expression (8), the refractive power of the first lens group becomes large. For this reason, amount of aberrations generated in the first lens group become large.

Moreover, in this case, since the refractive power of the first lens group does not become smaller than the refractive power of the second lens group, magnification at the telephoto end cannot be made large. To make the magnification at the telephoto end large, moving distance of the second lens group needs to be large.

However, if the moving distance of the second lens group is made large, large aberrations generated in the first lens group are further expanded in the second lens group. For this reason, since it is not possible to make the moving distance to the second lens group large, it is not possible to make the magnification at the telephoto end large.

It is preferable that the following conditional expression (7') be satisfied, instead of the conditional expression (7).

$$f1/fw<-6 \quad (7')$$

It is preferable that the following conditional expression (7") be satisfied, instead of the conditional expression (7).

$$f1/fw<-12 \quad (7'')$$

It is preferable that the following conditional expression (8') be satisfied, instead of the conditional expression (8).

$$f1/ft<-4 \quad (8')$$

It is preferable that the following conditional expression (8") be satisfied, instead of the conditional expression (8).

$$f1/ft<-8 \quad (8'')$$

In the objective optical system for an endoscope according to the present embodiment, it is preferable that the third lens group include a negative meniscus lens and a third cemented lens.

In the optical system with a long back focal length, the number of lenses and lens layout are limited in the third lens group. For this reason, in the third lens group, it is required that high imaging performance is achieved by disposing a small number of lenses appropriately.

In the objective optical system for an endoscope according to the present embodiment, the coma and the longitudinal chromatic aberration are corrected by the negative meniscus lens, and the chromatic aberration of magnification is corrected by the third cemented lens. With this configuration, it is possible to maintain high imaging performance with a small number of lenses.

In the objective optical system for an endoscope according to the present embodiment, it is preferable that following conditional expression (9) be satisfied:

$$0.4<|f3M/fc3|<4.0 \quad (9)$$

where f3M denotes a focal length of the negative meniscus lens, and fc3 denotes a focal length of the third cemented lens.

When a value falls below a lower limit value of conditional expression (9), a refractive power of the negative meniscus lens becomes large. For this reason, correction of the coma becomes excessive and correction of the chromatic aberration of magnification becomes inadequate. When a value exceeds upper limit value of conditional expression (9), the refractive power of the negative meniscus lens becomes small. For this reason, the correction of the coma becomes inadequate and the correction of the chromatic aberration of magnification becomes excessive.

It is preferable that the following conditional expression (9') be satisfied, instead of the conditional expression (9).

$$0.7<|f3M/fc3|<3.0 \quad (9')$$

It is preferable that the following conditional expression (9") be satisfied, instead of the conditional expression (9).

$$0.9<|f3M/fc3|<1.6 \quad (9'')$$

Examples of the objective optical system will be explained hereinafter in detail on the basis of the drawings. The present disclosure is not limited to the examples.

Sectional views of the lenses in the examples will be explained. FIG. 2A, FIG. 4A, FIG. 6A, and FIG. 8A are sectional views at the wide angle end. FIG. 2B, FIG. 4B, FIG. 6B, and FIG. 8B are sectional views at the telephoto end.

A first lens group is denoted by G1, a second lens group is denoted by G2, a third lens group is denoted by G3, an aperture stop is denoted by S, a prism is denoted by P, and an image plane (image pickup surface) is denoted by I.

Aberration diagrams of the examples will be explained.

FIG. 3A, FIG. 5A, FIG. 7A, and FIG. 9A illustrate spherical aberration (SA) at the wide angle end.

FIG. 3B, FIG. 5B, FIG. 7B, and FIG. 9B illustrate astigmatism (AS) at the wide angle end.

FIG. 3C, FIG. 5C, FIG. 7C, and FIG. 9C illustrate distortion (DT) at the wide angle end.

FIG. 3D, FIG. 5D, FIG. 7D, and FIG. 9D illustrate chromatic aberration of magnification (CC) at the wide angle end.

FIG. 3E, FIG. 5E, FIG. 7E, and FIG. 9E illustrate spherical aberration (SA) at the telephoto end.

FIG. 3F, FIG. 5F, FIG. 7F, and FIG. 9F illustrate astigmatism (AS) at the telephoto end.

FIG. 3G, FIG. 5G, FIG. 7G, and FIG. 9G illustrate distortion (DT) at the telephoto end.

FIG. 3H, FIG. 5H, FIG. 7H, and FIG. 9H illustrate chromatic aberration of magnification (CC) at the telephoto end.

In each of the aberration diagrams, the horizontal axis indicates an aberration quantity. With respect to the spherical aberration, the astigmatism, and the chromatic aberration of magnification, the unit of the aberration quantity is "mm". Moreover, with respect to the distortion, the unit of the aberration quantity is "%". FNO denotes an F number, and FIY denotes an image height with the unit of "mm" (millimeter). The unit of the wavelength of the aberration curve is "nm".

Example 1

An objective optical system for an endoscope of an example 1 will be explained hereinafter. The objective optical system for an endoscope of the example 1 includes, in order from an object side to an image side, a first lens group G1 having a negative refractive power, a second lens group G2 having a positive refractive power, and a third lens group G3 having a positive refractive power.

The first lens group G1 includes a planoconcave negative lens L1 of which the object side is a flat surface, a biconcave negative lens L2, a biconvex positive lens L3, a biconcave negative lens L4, a biconvex positive lens L5, and a positive meniscus lens L6 having a convex surface directed toward the image side. Here, the biconcave negative lens L2 and the biconvex positive lens L3 form a cemented lens. The biconcave negative lens L4 and the biconvex positive lens L5 form a cemented lens.

The second lens group G2 includes a biconvex positive lens L7, and a planoconcave negative lens L8 of which the object side is a flat surface. Here, the biconvex positive lens L7 and the planoconcave negative lens L8 form a cemented lens.

The third lens group G3 includes a negative meniscus lens L9 having a convex surface directed toward the object side, a biconvex positive lens L10, and a negative meniscus lens L11 having a convex surface directed to the image side. Here, the biconvex positive lens L10 and the negative meniscus lens L11 form a cemented lens.

An aperture stop S is disposed between the first lens group G1 and the second lens group G2. More specifically, the aperture stop S is disposed near a surface nearest to the object side of the second lens group G2.

The second lens group G2 moves at a time of changing magnification. The second lens group G2 moves toward an object side at a time of changing magnification from the wide angle end to the telephoto end. At the wide angle end, since a distant object is in focus, it is possible to perform the normal observation. At the telephoto end, since a close object is in focus, it is possible to perform the magnifying observation. The aperture stop S moves together with the second lens group G2.

A prism P is disposed on the image side of the third lens group G3.

Example 2

An objective optical system for an endoscope of an example 2 will be explained hereinafter. The objective optical system for an endoscope of the example 2 includes, in order from an object side to an image side, a first lens group G1 having a negative refractive power, a second lens group G2 having a positive refractive power, and a third lens group G3 having a positive refractive power.

The first lens group G1 includes a planoconcave negative lens L1 of which the object side is a flat surface, a planoconcave negative lens L2 of which the object side is a flat surface, a biconcave negative lens L3, a biconvex positive lens L4, a positive meniscus lens L5 having a convex surface directed to the image side, and a negative meniscus lens L6 having a convex surface directed to the image side. Here, the biconcave negative lens L3 and the biconvex positive lens L4 form a cemented lens. The positive meniscus lens L5 and the negative meniscus lens L6 form a cemented lens.

The second lens group G2 includes a biconvex positive lens L7, and a planoconcave negative lens L8 of which the object side is a flat surface. Here, the biconvex positive lens L7 and the planoconcave negative lens L8 form a cemented lens.

The third lens group G3 includes a negative meniscus lens L9 having a convex surface directed to the object side, a biconvex positive lens L10, and a negative meniscus lens L11 having a convex surface directed to the image side. Here, the biconvex positive lens L10 and the negative meniscus lens L11 form a cemented lens.

An aperture stop S is disposed between the second lens group G2 and the third lens group G3. More specifically, the aperture stop S is disposed near a surface nearest to the image side of the second lens group G2.

The second lens group G2 moves at a time of changing magnification. The second lens group G2 moves toward the object side at a time of changing magnification from the wide angle end to the telephoto end. At the wide angle end, since a distant object is in focus, it is possible to perform the normal observation. At the telephoto end, since a close object is in focus, it is possible to perform the magnifying observation. The aperture stop S moves together with the second lens group G2.

A prism P is disposed on the image side of the third lens group G3.

Example 3

An objective optical system for an endoscope of an example 3 will be explained hereinafter. The objective optical system for an endoscope of the example 3 includes, in order from an object side to an image side, a first lens group G1 having a negative refractive power, a second lens group G2 having a positive refractive power, and a third lens group G3 having a positive refractive power.

The first lens group G1 includes a planoconcave negative lens L1 of which the object side is a flat surface, a biconcave negative lens L2, a biconvex positive lens L3, a positive meniscus lens L4 having a convex surface directed to the image side, and a negative meniscus lens L5 having a convex surface directed to the image side. Here, the biconcave negative lens L2 and the biconvex positive lens L3 form a cemented lens. The positive meniscus lens L4 and the negative meniscus lens L5 form a cemented lens.

The second lens group G2 includes a biconvex positive lens L6, and a biconcave negative lens L7. Here, the biconvex positive lens L6 and the biconcave negative lens L7 form a cemented lens.

The third lens group G3 includes a negative meniscus lens L8 having a convex surface directed to the object side, a biconvex positive lens L9, and a negative meniscus lens L10 having a convex surface directed to the image side. Here, the biconvex positive lens L9 and the negative meniscus lens L10 form a cemented lens.

An aperture stop S is disposed between the first lens group G1 and the second lens group G2. More specifically, the aperture stop S is disposed near a surface nearest to the object side of the second lens group G2.

The second lens group G2 moves at a time of changing magnification. The second lens group G2 moves toward an object side at a time of changing magnification from the wide angle end to the telephoto end. At the wide angle end, since a distant object is in focus, it is possible to perform the normal observation. At the telephoto end, since a close object is in focus, it is possible to perform the magnifying observation. The aperture stop S moves together with the second lens group G2.

A prism P is disposed on the image side of the third lens group G3.

Example 4

An objective optical system for an endoscope of an example 4 will be explained hereinafter. The objective optical system for an endoscope of the example 4 includes, in order from an object side to an image side, a first lens group G1 having a negative refractive power, a second lens group G2 having a positive refractive power, and a third lens group G3 having a positive refractive power.

The first lens group G1 includes: a planoconcave negative lens L1 of which the object side is a flat surface, a biconcave negative lens L2, a biconvex positive lens L3, a positive meniscus lens L4 having a convex surface directed to the image side, and a negative meniscus lens L5 having a convex surface directed to the image side. Here, the biconcave negative lens L2 and the biconvex positive lens L3 form a cemented lens. The positive meniscus lens L4 and the negative meniscus lens L5 form a cemented lens.

The second lens group G2 includes a biconvex positive lens L6, and a negative meniscus lens L7 having a convex surface directed to the image side. Here, the biconvex positive lens L6 and the negative meniscus lens L7 form a cemented lens.

The third lens group G3 includes a biconcave negative lens L8, a biconvex positive lens L9, a negative meniscus lens L10 having a convex surface directed to the image side, and a planoconvex positive lens L11 of which the object side is a flat surface. Here, the biconvex positive lens L9 and the negative meniscus lens L10 form a cemented lens.

An aperture stop S is disposed between the first lens group G1 and the second lens group G2. More specifically, the aperture stop S is disposed near a surface nearest to the object side of the second lens group G2.

The second lens group G2 moves at a time of changing magnification. The second lens group G2 moves toward the object side at a time of changing magnification from the wide angle end to the telephoto end. At the wide angle end, since a distant object is in focus, it is possible to perform the normal observation. At the telephoto end, since a close object is in focus, it is possible to perform the magnifying observation. The aperture stop S moves together with the second lens group G2.

A prism P is disposed on the image side of the third lens group G3.

Numerical data of each example described above is shown below. In Surface data, r denotes radius of curvature of each lens surface, d denotes a distance between respective lens surfaces, nd denotes a refractive index of each lens for a d-line, vd denotes an Abbe number for each lens, and stop denotes an aperture stop.

In Zoom data, WE denotes a wide angle end, TE denotes a telephoto end, f denotes a focal length for the d-line, FNO. denotes an F number, IH denotes an image height.

Example 1

| Unit mm | | | | |
|---|---|---|---|---|
| Surface data | | | | |
| Surface no. | r | d | nd | vd |
| Object plane | ∞ | Variable | | |
| 1 | ∞ | 0.307 | 1.88300 | 40.76 |
| 2 | 1.3507 | 0.7487 | | |
| 3 | −5.3426 | 0.307 | 1.88300 | 40.76 |
| 4 | 2.1305 | 1.1027 | 1.48749 | 70.23 |
| 5 | −2.5097 | 0.3947 | | |
| 6 | −7.6146 | 0.3688 | 1.88300 | 40.76 |
| 7 | 1.7945 | 1.1137 | 1.80518 | 25.42 |
| 8 | −4.539 | 0.6058 | | |
| 9 | −3.721 | 0.5702 | 1.48749 | 70.23 |
| 10 | −2.1761 | Variable | | |
| 11(Stop) | ∞ | 0 | | |
| 12 | 2.4496 | 0.4386 | 1.48749 | 70.23 |
| 13 | −3.239 | 0.2807 | 1.74077 | 27.79 |
| 14 | ∞ | Variable | | |
| 15 | 4.5474 | 0.2807 | 1.81600 | 46.62 |
| 16 | 1.5642 | 0.1986 | | |
| 17 | 2.139 | 1.2632 | 1.51742 | 52.43 |
| 18 | −1.4887 | 0.2807 | 1.95906 | 17.47 |
| 19 | −1.9433 | 0.7334 | | |
| 20 | ∞ | 5.2193 | 1.63854 | 55.38 |
| 21 | ∞ | 0 | | |
| Image plane | ∞ | | | |

| Zoom data | | |
|---|---|---|
| | WE | TE |
| f | 0.97 | 1.11 |
| Fno | 3.999 | 4.509 |
| IH | 1.00 | |
| d0 | 17.5 | 1.75 |
| d10 | 1.92279 | 0.6070 |
| d14 | 0.21050 | 1.52629 |

Example 2

| Unit mm | | | | |
|---|---|---|---|---|
| Surface data | | | | |
| Surface no. | r | d | nd | vd |
| Object plane | ∞ | Variable | | |
| 1 | ∞ | 0.3067 | 1.88300 | 40.76 |
| 2 | 1.2846 | 0.4908 | | |
| 3 | ∞ | 0.3067 | 1.88300 | 40.76 |
| 4 | 2.8066 | 0.7535 | | |
| 5 | −6.0044 | 0.2461 | 1.88300 | 40.76 |
| 6 | 2.0069 | 0.829 | 1.80518 | 25.42 |
| 7 | −3.0353 | 1.25 | | |
| 8 | −7.3199 | 0.5043 | 1.48749 | 70.23 |
| 9 | −1.9686 | 0.2805 | 1.75500 | 52.32 |
| 10 | −2.3069 | Variable | | |
| 11 | 2.5702 | 0.4382 | 1.48749 | 70.23 |
| 12 | −3.62 | 0.2805 | 1.74077 | 27.79 |
| 13 | ∞ | 0.0222 | | |
| 14(Stop) | ∞ | Variable | | |
| 15 | 3.7407 | 0.2805 | 1.88300 | 40.76 |
| 16 | 1.6285 | 0.2 | | |
| 17 | 2.2311 | 0.9938 | 1.51742 | 52.43 |
| 18 | −1.8819 | 0.2805 | 1.95906 | 17.47 |
| 19 | −2.327 | 0.7326 | | |
| 20 | ∞ | 5.2147 | 1.63854 | 55.38 |
| 21 | ∞ | 0 | | |
| Image plane | ∞ | | | |

| Zoom data | | |
|---|---|---|
| | WE | TE |
| f | 0.93 | 1.05 |
| Fno | 3.998 | 4.454 |
| IH | 1.00 | |
| d0 | 17.5 | 1.75 |
| d10 | 1.53814 | 0.2235 |
| d14 | 0.18400 | 1.49864 |

Example 3

| Unit mm | | | | |
|---|---|---|---|---|
| Surface data | | | | |
| Surface no. | r | d | nd | vd |
| Object plane | ∞ | Variable | | |
| 1 | ∞ | 0.3681 | 1.88300 | 40.76 |
| 2 | 1.2615 | 1.2912 | | |
| 3 | −2.2203 | 0.3205 | 1.88300 | 40.76 |
| 4 | 2.4126 | 1.0395 | 1.80518 | 25.42 |

-continued

Unit mm

| | | | | |
|---|---|---|---|---|
| 5 | −2.894 | 1.5151 | | |
| 6 | −5.9112 | 0.6278 | 1.51633 | 64.14 |
| 7 | −2.6222 | 0.3366 | 1.88300 | 40.76 |
| 8 | −2.7053 | Variable | | |
| 9(Stop) | ∞ | 0 | | |
| 10 | 2.6146 | 0.4196 | 1.48749 | 70.23 |
| 11 | −3.4652 | 0.3366 | 1.74077 | 27.79 |
| 12 | 433.6892 | Variable | | |
| 13 | 12.354 | 0.3366 | 1.48749 | 70.23 |
| 14 | 2.0603 | 0.2092 | | |
| 15 | 3.0328 | 0.9456 | 1.51742 | 52.43 |
| 16 | −2.7662 | 0.3366 | 1.95906 | 17.47 |
| 17 | −3.592 | 1.0222 | | |
| 18 | ∞ | 6.2581 | 1.51633 | 64.14 |
| 19 | ∞ | 0 | | |
| Image plane | ∞ | | | |

Zoom data

| | WE | TE |
|---|---|---|
| f | 1.18 | 1.35 |
| Fno | 4.668 | 5.144 |
| IH | 1.20 | |
| d0 | 20 | 2.1 |
| d8 | 1.89287 | 0.31520 |
| d12 | 0.25250 | 1.83017 |

Example 4

Unit mm

Surface data

| Surface no. | r | d | nd | vd |
|---|---|---|---|---|
| Object plane | ∞ | Variable | | |
| 1 | ∞ | 0.31 | 1.88300 | 40.76 |
| 2 | 1.185 | 1.4966 | | |
| 3 | −2.5987 | 0.2782 | 1.88300 | 40.76 |
| 4 | 1.8543 | 0.8726 | 1.80518 | 25.42 |
| 5 | −3.1589 | 0.4373 | | |
| 6 | −4.4343 | 0.5238 | 1.51633 | 64.14 |
| 7 | −2.0077 | 0.2805 | 1.88300 | 40.76 |
| 8 | −2.1264 | Variable | | |
| 9(Stop) | ∞ | 0 | | |
| 10 | 2.2209 | 0.4113 | 1.48749 | 70.23 |
| 11 | −2.6888 | 0.2805 | 1.74077 | 27.79 |
| 12 | −16.1353 | Variable | | |
| 13 | −9.7228 | 0.2805 | 1.48749 | 70.23 |
| 14 | 1.9879 | 0.1414 | | |
| 15 | 2.9777 | 0.7659 | 1.51742 | 52.43 |
| 16 | −1.6381 | 0.2805 | 1.95906 | 17.47 |
| 17 | −2.4236 | 0.0542 | | |
| 18 | ∞ | 0.2828 | 1.74400 | 44.78 |
| 19 | −8.2626 | 0.6812 | | |
| 20 | ∞ | 5.2147 | 1.63854 | 55.38 |
| 21 | ∞ | 0 | | |
| Image plane | ∞ | | | |

Zoom data

| | WE | TE |
|---|---|---|
| f | 0.98 | 1.17 |
| Fno | 4.433 | 5.034 |
| IH | 1.00 | |
| d0 | 17.3 | 1.75 |
| d8 | 1.57194 | 0.25730 |
| d12 | 0.21030 | 1.52494 |

Values of conditional expressions in each example are given below. '-' (hyphen) indicates that there is no corresponding arrangement.

| | Example1 | Example2 | Example3 | Example4 |
|---|---|---|---|---|
| (1)(Lb × f3)/(Lf × f12) | 3.0 | 3.6 | 5.0 | 4.5 |
| (2)f3/fw | 6.1 | 6.9 | 8.3 | 6.7 |
| (3)|f1/f3| | 4.0 | 2.6 | 1.0 | 0.9 |
| (4)|f1/f2| | 3.0 | 2.1 | 1.1 | 1.0 |
| (5)|fc2/fc1| | 2.7 | 0.8 | 0.6 | 0.5 |
| (6)f3/ft | 5.4 | 6.1 | 7.3 | 5.6 |
| (7)f1/fw | −24.7 | −18.3 | −8.3 | −6.1 |
| (8)f1/ft | −21.7 | −16.2 | −7.2 | −5.1 |
| (9)|f3M/fc3| | 1.2 | 1.3 | 1.4 | — |

Values of parameters are given below.

| | Example1 | Example2 | Example3 | Example4 |
|---|---|---|---|---|
| Lb | 7.98 | 7.70 | 9.11 | 7.70 |
| f3 | 5.93 | 6.46 | 9.85 | 6.55 |
| Lf | 8.37 | 7.43 | 8.40 | 6.67 |
| f12 | 1.91 | 1.87 | 2.12 | 1.70 |
| fw | 0.97 | 0.93 | 1.18 | 0.98 |
| f1 | −23.96 | −17.07 | −9.77 | −5.90 |
| f2 | 7.97 | 8.09 | 8.65 | 5.77 |
| fc1 | −9.51 | 9.39 | −15.19 | −14.52 |
| fc2 | 25.87 | 7.15 | 8.37 | 6.92 |
| ft | 1.11 | 1.05 | 1.35 | 1.17 |
| f3M | −3.05 | −3.48 | −5.13 | −3.36 |
| fc3 | 2.51 | 2.63 | 3.77 | 3.41 |

According to the present disclosure, it is possible to provide an objective optical system with a long back focal length, capability of focusing, and favorably corrected aberrations, and an image pickup apparatus, an endoscope, and an endoscope system that include the objective optical system.

The present disclosure is suitable for an objective optical system with a long back focal length, capability of focusing, and favorably corrected aberrations, and an image pickup apparatus, an endoscope, and an endoscope system that include the objective optical system.

What is claimed is:

1. An objective optical system comprising, in order from an object side:
   a first lens group having a negative refractive power,
   a second lens group having a positive refractive power,
   a third lens group having a positive refractive power,
   wherein:
   the second lens group includes an aperture stop and moves at a time of changing magnification, and
   following conditional expressions (1), (3) and (4) are satisfied:

$$1 < (Lb \times f3)/(Lf \times f12) < 9 \quad (1);$$

$$1 < |f1/f3| < 20 \quad (3); \text{ and}$$

$$1 < |f1/f2| < 14 \quad (4)$$

where
Lb denotes a distance from a surface nearest to the object side of the third lens group to an image plane,
f3 denotes a focal length of the third lens group,
Lf denotes a distance from a surface nearest to the object side of the first lens group to the surface nearest to the object side of the third lens group, f12 denotes a combined focal length of the first lens group and the second lens group at a wide angle end, f1 denotes a focal length of the first lens group, and f2 denotes a focal length of the second lens group.

2. The objective optical system according to claim 1, wherein following conditional expression (2) is satisfied:

$$4 < f3/fw < 24 \quad (2)$$

where fw denotes a focal length of the objective optical system at the wide angle end.

3. The objective optical system according to claim 1, wherein the first lens group includes at least two cemented lenses.

4. The objective optical system according to claim 3, wherein the first lens group includes a first cemented lens and a second cemented lens, the first cemented lens is positioned nearest to the object side, the second cemented lens is positioned nearest to the image side, and following conditional expression (5) is satisfied:

$$0.2 < |fc2/fc1| < 6.0 \quad (5)$$

where fc1 denotes a focal length of the first cemented lens, and fc2 denotes a focal length of the second cemented lens.

5. The objective optical system according to claim 1, wherein following conditional expression (6) is satisfied:

$$2 < f3/ft < 20 \quad (6)$$

where ft denotes a focal length of the objective optical system at a telephoto end.

6. The objective optical system according to claim 1, wherein following conditional expressions (7) and (8) are satisfied:

$$f1/fw < -3 \quad (7); \text{ and}$$

$$f1/ft < -2 \quad (8)$$

where fw denotes a focal length of the objective optical system at the wide angle end, and ft denotes a focal length of the objective optical system at a telephoto end.

7. The objective optical system according to claim 1, wherein the third lens group includes a negative meniscus lens and a third cemented lens.

8. The objective optical system according to claim 7, wherein following conditional expression (9) is satisfied:

$$0.4 < |f3M/fc3| < 4.0 \quad (9)$$

where f3M denotes a focal length of the negative meniscus lens, and fc3 denotes a focal length of the third cemented lens.

9. An image pickup apparatus comprising the objective optical system according to claim 1.

10. An endoscope comprising the objective optical system according to claim 1.

11. An endoscope system comprising:

the objective optical system according to claim 1, and an image processor.

* * * * *